(12) United States Patent
Yamashita

(10) Patent No.: US 10,912,460 B2
(45) Date of Patent: Feb. 9, 2021

(54) OPHTHALMIC IMAGING APPARATUS AND CONTROL METHOD THEREOF

(71) Applicant: CANON KABUSHIKI KAISHA, Tokyo (JP)

(72) Inventor: Risa Yamashita, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/791,528

(22) Filed: Oct. 24, 2017

(65) Prior Publication Data

US 2018/0116511 A1 May 3, 2018

(30) Foreign Application Priority Data

Oct. 31, 2016 (JP) ................. 2016-213551

(51) Int. Cl.
*A61B 3/14* (2006.01)
*A61B 3/10* (2006.01)
*A61B 3/00* (2006.01)

(52) U.S. Cl.
CPC .............. *A61B 3/14* (2013.01); *A61B 3/0025* (2013.01); *A61B 3/0041* (2013.01); *A61B 3/102* (2013.01)

(58) Field of Classification Search
None
See application file for complete search history.

(56) References Cited

U.S. PATENT DOCUMENTS

| | | | |
|---|---|---|---|
| 9,456,748 B2 | 10/2016 | Imamura | |
| 9,566,001 B2 | 2/2017 | Katashiba | |
| 9,615,736 B2 | 4/2017 | Yamashita | |
| 9,820,648 B2 | 11/2017 | Ota et al. | |
| 2007/0147707 A1* | 6/2007 | Coste-Maniere | G06T 7/60 382/298 |
| 2013/0215384 A1* | 8/2013 | Hirose | A61B 3/1025 351/206 |
| 2013/0229620 A1 | 9/2013 | Hammer et al. | |

(Continued)

FOREIGN PATENT DOCUMENTS

| | | |
|---|---|---|
| JP | 2010-035950 A | 2/2010 |
| JP | 2012-192261 A | 10/2012 |

(Continued)

OTHER PUBLICATIONS

Sep. 1, 2020 Japanese Official Action in Japanese Patent Appln. No. 2016-213551.

*Primary Examiner* — Darryl J Collins
*Assistant Examiner* — Journey F Sumlar
(74) *Attorney, Agent, or Firm* — Venable LLP

(57) ABSTRACT

Provided is a system includes: an image forming portion 161, which forms an image related to the imaging of the eye to be inspected E, based on return light of measuring light from the eye to be inspected E; a display control portion 162 which performs control to display the image formed by the image forming portion 161 on a display portion 180; and an area setting portion 163, which sets one of imaging areas, a first imaging area, which is a specified rectangular area, and a second imaging area, which is narrower than the specified rectangular area and includes a curved part based on a maximum imageable area determined based on the focus adjustment performed by the focus adjusting unit 134, as an imaging area of the eye to be inspected E, according to the maximum imageable area.

40 Claims, 2 Drawing Sheets

(56) References Cited

U.S. PATENT DOCUMENTS

| | | |
|---|---|---|
| 2014/0185009 A1 | 7/2014 | Imamura |
| 2015/0002813 A1 | 1/2015 | Ota et al. |
| 2016/0089024 A1 | 3/2016 | Katashiba |

FOREIGN PATENT DOCUMENTS

| | | |
|---|---|---|
| JP | 2014-097191 A | 5/2014 |
| JP | 2014-128366 A | 7/2014 |
| JP | 2014-140489 A | 8/2014 |
| JP | 2015-102537 A | 6/2015 |
| JP | 2016-049158 A | 4/2016 |
| JP | 2016-067551 A | 5/2016 |
| WO | 2014/207904 A1 | 12/2014 |
| WO | 2014/207904 A9 | 11/2015 |

\* cited by examiner

OPHTHALMIC IMAGING APPARATUS AND CONTROL METHOD THEREOF

BACKGROUND OF THE INVENTION

Field of the Invention

The present invention relates to an ophthalmic imaging apparatus which images an eye to be inspected and a control method thereof.

Description of the Related Art

Currently, as an ophthalmic imaging apparatus, an optical coherence tomography apparatus (hereinafter, referred to as "OCT apparatus") with optical coherence tomography (OCT) using interference of light waves is widely used for diagnosis or the like in the field of ophthalmology. This type of OCT apparatus splits low-coherence light from a light source into measuring light and reference light and applies the measuring light to an eye to be inspected. Thereafter, the OCT apparatus causes backscattered light (hereinafter, referred to as "return light") of the measuring light obtained from the eye to be inspected and reference light to interfere with each other and thereby is able to acquire a tomographic image in a certain position of the eye to be inspected from interference light obtained by the interference.

It is known that the use of a variable wavelength light source in this OCT apparatus enables acquisition of a high depth-of-field image (Japanese Patent Application Laid-Open No. 2015-102537). When an attempt is made to acquire a high depth-of-field image, an image of the fundus portion to the periphery of the equator of an eye to be inspected can be obtained at a time depending on the eye to be inspected.

In the conventional ophthalmic imaging apparatus, when an attempt is made to enlarge the range of imaging the eye to be inspected at a time, the imaging area for acquiring the image is significantly limited in relation to the maximum imageable area.

SUMMARY OF THE INVENTION

The present invention provides a mechanism enabling acquisition of a wider range of image in relation to the maximum imageable area in imaging an eye to be inspected.

According to an aspect of the present invention, there is provided an ophthalmic imaging apparatus including: a scanning unit which performs two-dimensional scanning on an eye to be inspected with measuring light based on light emitted from a light source; a focus adjusting unit which adjusts a focus in the measuring light to the eye to be inspected; an image forming unit which forms an image related to imaging of the eye to be inspected, based on return light of the measuring light from the eye to be inspected; a display control unit which performs control to display the image formed by the image forming unit on a display portion; and a setting unit which sets one of imaging areas in accordance with a maximum imageable area determined based on the focus adjustment performed by the focus adjusting unit, a first imaging area, which is a specified rectangular area, and a second imaging area, which is narrower than the specified rectangular area and includes a curved part based on the maximum imageable area, as an imaging area of the eye to be inspected.

Moreover, according to another aspect of the present invention, there is provided a control method of the aforementioned ophthalmic imaging apparatus.

Further features of the present invention will become apparent from the following description of exemplary embodiments with reference to the attached drawings.

According to the present invention, a wider range of image is able to be acquired in relation to the maximum imageable range in imaging an eye to be inspected.

DESCRIPTION OF THE EMBODIMENTS

Preferred embodiments of the present invention will now be described in detail with reference to the accompanying drawings.

Figure 1:
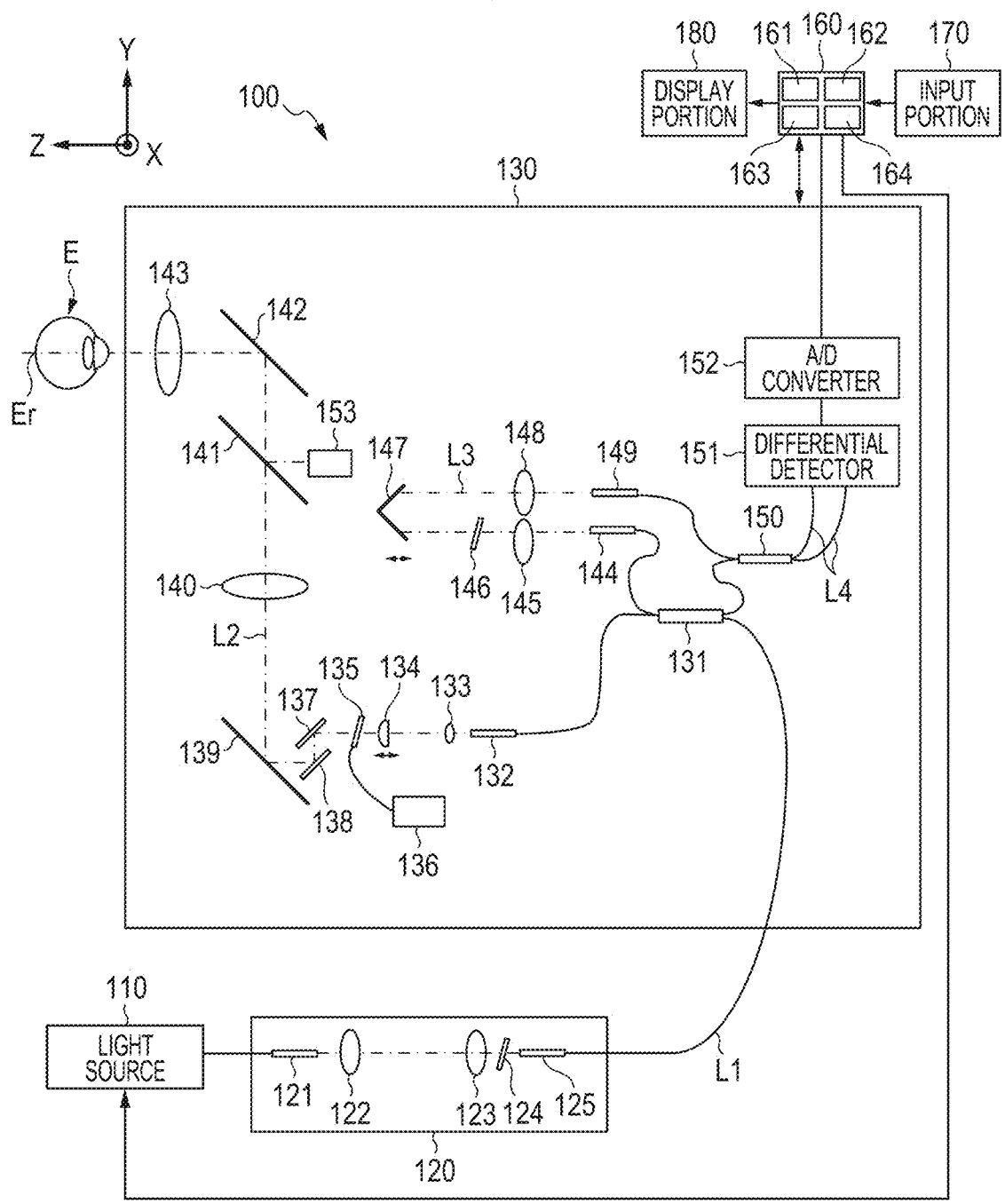
FIG. 1 is a diagram illustrating an example of an outline configuration of an ophthalmic imaging apparatus according to an embodiment of the present invention.

FIG. 1 is a diagram illustrating an example of an outline configuration of an ophthalmic imaging apparatus 100 according to an embodiment of the present invention. This ophthalmic imaging apparatus 100 is used to image an eye to be inspected E (specifically, in this embodiment, the fundus Er of the eye to be inspected E). In addition, the eye to be inspected E illustrated in FIG. 1 is a cross section of the eyeball viewed from the side. In addition, the aforementioned OCT apparatus is applicable to the ophthalmic imaging apparatus 100, for example.

As illustrated in FIG. 1, the ophthalmic imaging apparatus 100 is configured to include a light source 110, a light amount adjusting portion 120, an optical head portion 130, a control and processing portion 160, an input portion 170, and a display portion 180.

In the ophthalmic imaging apparatus 100, the respective optical elements of the optical head portion 130 constitute the optical paths L1 to L4. In this respect, light passing through the optical paths L1 to L4 includes light propagating through an optical fiber and light propagating in the air via an optical member.

The light source 110 and the light amount adjusting portion 120 are arranged in the optical path L1.

The light source 110 emits light on the basis of the control of the control and processing portion 160.

The light amount adjusting portion 120 adjusts the amount of light emitted from the light source 110. The light amount adjusting portion 120 includes a fiber end 121, which propagates light into the air, optical members 122, 123, and 124 for adjusting the amount of light emitted from the fiber end 121, and a fiber end 125 for guiding the light having passed through the optical member 124 to the optical head portion 130.

Subsequently, the optical head portion 130 will be described.

The coupler 131 is a light dividing unit, which divides (splits) the light output from the light amount adjusting portion 120 into measuring light and reference light. The measuring light obtained by the coupler 131 passes through the optical path L2 and is guided to the fundus Er of the eye to be inspected E.

The optical path L2 related to the measuring light will be described below.

Specifically, the measuring light divided by the coupler 131 propagates into the air by the fiber end 132 and reaches the shutter 135 via the optical members 133 and 134. Note that the optical member 134 is a focus adjusting unit, which is used to adjust a focus for correcting the ametropia of the eye to be inspected E in the measuring light applied to the fundus Er of the eye to be inspected E and specifically is a focus lens. The optical member 134 is configured so as to be movable in position in the directions indicated by the arrows in the drawing on the basis of the control of the control and processing portion 160. Moreover, the shutter 135 is driven by the shutter drive mechanism 136 on the basis of the control of the control and processing portion 160 to control the on-off operation to apply the measuring light to the eye to be inspected E.

The measuring light having passed through the shutter 135 reaches galvanometer scanners 137 and 138. The galvanometer scanners 137 and 138 constitute a scanning unit, which performs two-dimensional scanning on the fundus Er of the eye to be inspected E with the measuring light on the basis of the control of the control and processing portion 160. In this embodiment, the galvanometer scanners 137 and 138 perform scan the fundus Er of the eye to be inspected E with the measuring light in the X direction and in the Y direction, respectively, to perform the two-dimensional scanning on the fundus Er with the measuring light.

The measuring light having traveled through the galvanometer scanners 137 and 138 is guided to the fundus Er of the eye to be inspected E by the objective lens 143 via a mirror 139, a relay lens 140, a dichroic mirror 141, and a mirror 142. Note that, in this embodiment, the objective lens 143 (and further the relay lens 140) is assumed to be a substantially circular lens.

The measuring light having reached the fundus Er of the eye to be inspected E diffuses, reflects, or the like on the fundus Er and then becomes return light. The return light of the measuring light then follows the optical path L2 to return to the coupler 131 and thereafter reaches a coupler 150.

Subsequently, the optical path L3 related to the reference light will be described below.

Specifically, the reference light obtained by the coupler 131 propagates into the air by the fiber end 144 and then reaches a reference mirror 147 for use in changing the optical path length of the optical path L3 via an optical member 145 and an optical member 146 for adjusting the light amount. This reference mirror 147 is configured to be movable in position in the directions indicated by the arrows in the drawing on the basis of the control of the control and processing portion 160. The reference light reflected on the reference mirror 147 is guided from a fiber end 149 to the coupler 150 via an optical member 148.

The coupler 150 is a combining unit, which combines the return light of the measuring light guided from the coupler 131 with the reference light guided from the fiber end 149. The interference light combined by the coupler 150 splits and passes through the optical path L4 so as to be guided to a differential detector 151. The differential detector 151 detects the interference light as an OCT interference signal, which is an electrical signal. The A/D converter 152 converts the analog OCT interference signal obtained by the differential detector 151 to a digital OCT interference signal and then outputs it to the control and processing portion 160.

In addition, the optical head portion 130 is also provided with an observation optical system 153 for observing the fundus Er of the eye to be inspected E. The fundus reflection light of the fundus Er irradiated with illumination light, which is not illustrated, is split from the optical path L2 by the dichroic mirror 141 and guided to the observation optical system 153. As described later, an observation image, which is formed based on the fundus reflection light received by the observation optical system 153, is displayed on the display portion 180.

The control and processing portion 160 integrally controls the operation of the ophthalmic imaging apparatus 100 on the basis of input information or the like input from the input portion 170, for example, and performs various kinds of processing. For example, the control and processing portion 160 controls the light source 110 or the optical head portion 130 on the basis of the imaging condition input from the input portion 170. The control and processing portion 160 includes an image forming portion 161, a display control portion 162, an area setting portion 163, and a light amount control portion 164.

The image forming portion 161 forms an image of the fundus Er of the eye to be inspected E on the basis of the return light of the measuring light from the fundus Er of the eye to be inspected E (specifically, the return light having passed through the substantially circular lenses such as the objective lens 143 and the like and then having reached the coupler 131 via the galvanometer scanners 137 and 138). In this embodiment, the image forming portion 161 performs various kinds of signal processing (for example, frequency analysis processing or the like such as Fourier transform) for the OCT interference signal output from the A/D converter 152 to form a tomographic image as the image. Furthermore, the image forming portion 161 forms an observation image on the basis of the observation light output from the observation optical system 153. In this embodiment, the image forming portion 161 forms a fundus front image as the observation image.

The display control portion 162 performs control to display various images including the image and the observation image formed by the image forming portion 161 or various kinds of information such as, for example, imaging conditions, information related to a subject, or the like on the display portion.

The area setting portion 163 sets a two-dimensional scanning area scanned by the galvanometer scanners 137 and 138, the maximum imageable area, a user-specified area specified as an area desired by a user for its imaging, an imaging area of the fundus Er of the eye to be inspected E to be taken as an image by the image forming portion 161, and the like.

The light amount control portion 164 controls the light amount of the light emitted from the light source 110.

The input portion 170 inputs, for example, input information operationally input by a user or input information input from an external device, which is not illustrated, via a communication line to the control and processing portion 160.

The display portion 180 displays the aforementioned various images or various kinds of information on the basis of the control of the control and processing portion 160 (specifically, the display control portion 162).

The following describes the detailed processing of the respective portions 161 to 164 provided in the control and processing portion 160.

Figure 2:
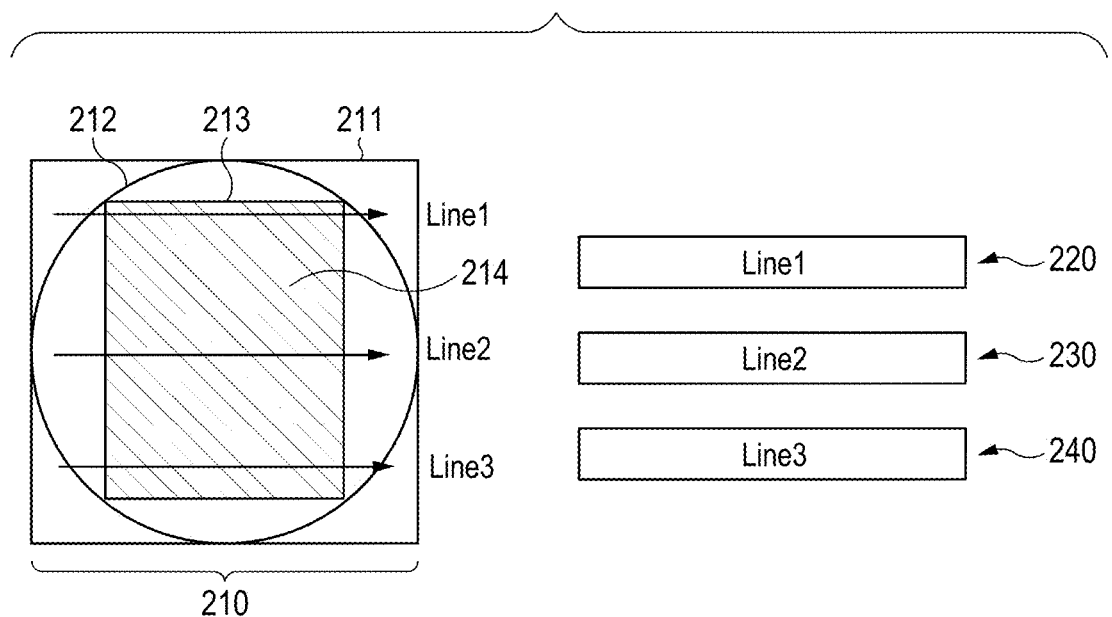
FIG. 2 is a diagram illustrating an example of a first display screen displayed in a display portion by the display control portion of FIG. 1.

FIG. 2 is a diagram illustrating an example of a first display screen displayed on the display portion 180 by the display control portion 162 of FIG. 1.

The first display screen illustrated in FIG. 2 displays various areas 211 to 214, which have been set by the area setting portion 163, in the display region 210 by the display control of the display control portion 162.

Specifically, the two-dimensional scanning area 211 represents an area to be scanned in the two-dimensional scanning with the measuring light in an X direction, which is the horizontal direction, and in a Y direction, which is the vertical direction, on the fundus Er by using the galvanometer scanners 137 and 138. In this specification, it is assumed that raster scanning is performed as the two-dimensional scanning with the X direction (horizontal direction) as a main scanning direction and the Y direction (vertical direction) as a sub scanning direction.

The maximum imageable area 212 is an area determined based on the focus adjustment performed by the optical member 134, which is a focus adjusting unit. More specifically, the maximum imageable area 212 is an area determined by the position of the optical member 134 based on the position of the reference mirror 147, and the information thereof is assumed to be previously stored in the control and processing portion 160 for each operating position of the galvanometer scanners 137 and 138. Moreover, the maximum imageable area 212 is a substantially circular area based on the shape of the substantially circular lens such as the objective lens 143 or the like.

The user-specified area 213 represents a rectangular area specified as an area desired to be imaged via the input portion 170 by the user.

The imaging area 214 represents an imaging area (shaded portion) of the fundus Er of the eye to be inspected E to be taken as an image by the image forming portion 161.

In the example illustrated in FIG. 2, the user-specified area 213 is included in the maximum imageable area 212. Therefore, the area setting portion 163 sets the imaging area 214 (a first imaging area), which is the same rectangular area as the user-specified area 213, as the imaging area of the fundus Er of the eye to be inspected E.

Note that, with the two-dimensional scanning area 211, for example, as the entire area of the image displayed on the screen, it is assumed that the display control portion 162 displays the observation image (a fundus front image) formed by the image forming portion 161 in the area in this embodiment. In other words, the display control portion 162 performs control to superimpose the imaging area 214 (and further the areas 211 to 213), which has been set by the area setting portion 163, on the observation image and then to display the image on the display portion 180.

Furthermore, in the first display screen illustrated in FIG. 2, the display control portion 162 displays the images (tomographic images) 220 to 240, which are obtained by scanning in the main scanning direction (X direction [horizontal direction]) on the imaging area 214 with the galvanometer scanners 137 and 138, on the display portion 180. Specifically, the example illustrated in FIG. 2 provides an illustration of displaying the image 230, which is obtained in the center position Line 2 in the sub scanning direction (Y direction [vertical direction]) of the imaging area 214, and the images 220 and 240, which are obtained in the both end positions Line 1 and Line 3 in the sub scanning direction of the imaging area 214. These images 220 to 240 coincide with the user-specified area 213, where the imaging area 214 (the first imaging area) is a rectangular area, and therefore all data represents the fundus Er that is to be imaged.

Figure 3:
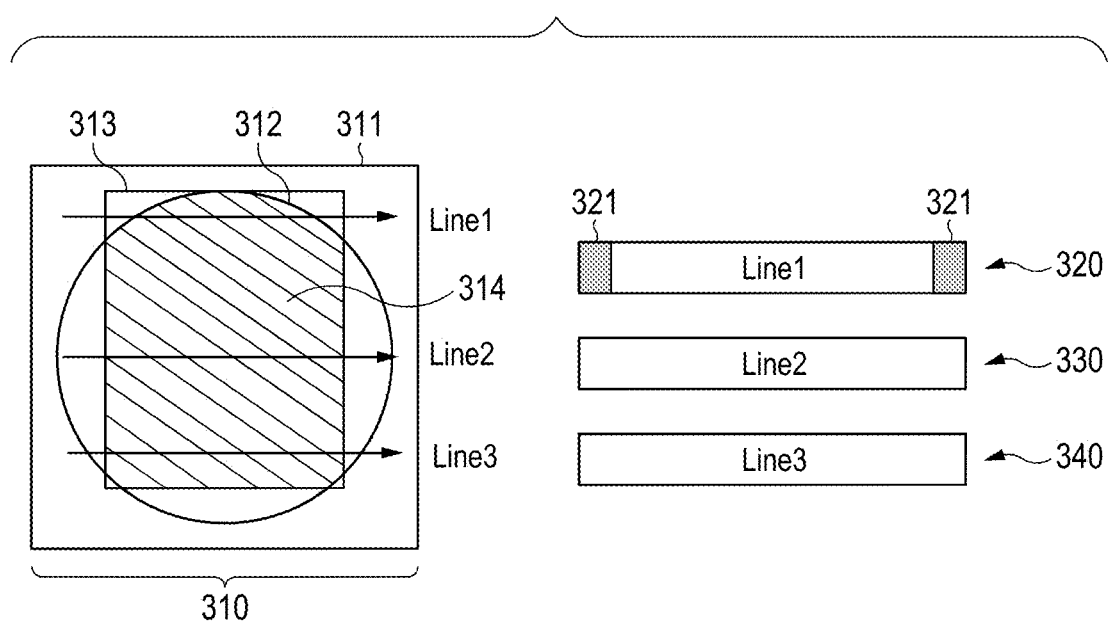
FIG. 3 is a diagram illustrating an example of a second display screen displayed on the display portion by the display control portion of FIG. 1.

FIG. 3 is a diagram illustrating an example of a second display screen displayed on the display portion 180 by the display control portion 162 of FIG. 1.

The second display screen illustrated in FIG. 3 displays various areas 311 to 314, which have been set by the area setting portion 163, in the display region 310 by the display control of the display control portion 162.

Specifically, the two-dimensional scanning area 311 represents an area to be scanned in the two-dimensional scanning with the measuring light in the X direction, which is the horizontal direction, and in the Y direction, which is the vertical direction, on the fundus Er by using the galvanometer scanners 137 and 138, similarly to the two-dimensional scanning area 211 illustrated in FIG. 2. In this specification, it is assumed that raster scanning is performed as the two-dimensional scanning with the X direction (horizontal direction) as the main scanning direction and the Y direction (vertical direction) as the sub scanning direction.

The maximum imageable area 312 is an area determined based on the focus adjustment performed by the optical member 134, which is a focus adjusting unit. More specifically, the maximum imageable area 312 is an area determined by the position of the optical member 134 based on the position of the reference mirror 147, and the information thereof is assumed to be previously stored in the control and processing portion 160 for each operating position of the galvanometer scanners 137 and 138. Moreover, the maximum imageable area 312 is a substantially circular area based on the shape of the substantially circular lens such as the objective lens 143 or the like. More specifically, the maximum imageable area 312 is smaller than the maximum imageable area 212 illustrated in FIG. 2 since the optical member 134 moves in position from the state illustrated in FIG. 2 due to input information input by the user, for example.

The user-specified area 313 represents a rectangular area specified as an area desired to be imaged via the input portion 170 by the user, similarly to the user-specified area 213 illustrated in FIG. 2.

The imaging area 314 represents an imaging area (shaded portion) of the fundus Er of the eye to be inspected E to be taken as an image by the image forming portion 161.

In the example illustrated in FIG. 3, the user-specified area 313 has parts not included in the maximum imageable area 312. Therefore, it is illustrated that the area setting portion 163 sets the imaging area 314 (a second imaging area), which is narrower than the user-specified area 313 which is the rectangular area and includes a curved (arc) part based on the maximum imageable area 312, as the imaging area of the fundus Er of the eye to be inspected E.

Note that, with the two-dimensional scanning area 311, for example, as the entire area of the image displayed on the screen, it is assumed that the display control portion 162 displays the observation image (a fundus front image) formed by the image forming portion 161 in the area in this embodiment. In other words, the display control portion 162 performs control to superimpose the imaging area 314 (and further the areas 311 to 313), which has been set by the area setting portion 163, on the observation image and then to display the image on the display portion 180.

Furthermore, in the second display screen illustrated in FIG. 3, the display control portion 162 displays the images (tomographic images) 320 to 340, which are obtained by scanning in the main scanning direction (X direction [horizontal direction]) on the imaging area 314 with the galvanometer scanners 137 and 138, on the display portion 180. Specifically, the example illustrated in FIG. 3 provides an illustration of displaying the image 330, which is obtained in the center position Line 2 in the sub scanning direction (Y direction [vertical direction]) of the imaging area 314, and the images 320 and 340, which are obtained in the both end positions Line 1 and Line 3 in the sub scanning direction of the imaging area 314. The respective positions Line 2 and Line 3 of the images 330 and 340 among the images are included in the maximum imageable area 312, and therefore all data thereof represents the fundus Er that is to be imaged.

On the other hand, the imaging area 314 has parts cut off by the arc of the maximum imageable area 312, and therefore both end portions of the imaging area 314 in the position Line 1 are not included in the maximum imageable area 312. Accordingly, in the image 320, the data of only portions included in the maximum imageable area 312 represents the fundus Er that is to be imaged. In other words, in the image 320, the portions 321 outside the imaging area 314 in the user-specified area 313, which is a rectangular area, do not represent the fundus Er that is to be imaged. In this case, for example, the image forming portion 161 forms an image 320 with the portions 321 outside the imaging area 314 in the user-specified area 313, which is a rectangular area, masked with predetermined values.

This embodiment, however, is not limited to the mode in which the portions 321 are masked with the predetermined values. For example, in the case where each portion 321 is larger in size than the predetermined threshold value, the image forming portion 161 may be configured to form the image 320 based on the measuring light of the portion 321 in regard to the portion 321. With this processing, an image 320 with less sense of discomfort can be formed.

Moreover, in the case where the imaging area 314 illustrated in FIG. 3 is set, the light amount control portion 164 performs the control of decreasing the light amount of light (including turning off the light) emitted from the light source 110 at least during a part of the period during which, for example, the galvanometer scanners 137 and 138 scan the area outside the imaging area 314. This enables a reduction in the light amount of the measuring light in scanning the portion not acquired as the image, thereby enabling a decrease in an influence of light unrequired for imaging on the eye to be inspected E.

Furthermore, the control and processing portion 160 may operate the shutter 135 to perform imaging in the case where, for example, the galvanometer scanners 137 and 138 scan an area outside the imaging area 314.

Moreover, in this embodiment, the area setting portion 163 is allowed to set the user-specified area 313, which is a rectangular area, until the user-specified area 313 circumscribes the maximum imageable area 312 in the case where the galvanometer scanners 137 and 138 perform the two-dimensional scanning (raster scanning) on the fundus Er.

Furthermore, although the description has been made by giving the examples of FIGS. 2 and 3 in which the display control portion 162 displays three images aligned, four or more images may be displayed aligned in this embodiment.

Still further, although the description has been made on the case where raster scanning is performed as the two-dimensional scanning in this embodiment, the present invention is not limited thereto. For example, radial scanning may be performed, instead. In addition, both of the raster scanning and the radial scanning may be made applicable to the two-dimensional scanning, so that the control and processing portion 160 performs imaging by selecting either one of the scanning methods on the basis of input information input from the input portion 170.

The image 320 illustrated in FIG. 3 may change the display magnification of the image 320 according to the portions 321 so that the data display region is equal to those of other images 330 and 340, for example. Moreover, the display region on the display screen may be changed according to the regions of the respective images.

Furthermore, although a Mach-Zehnder interferometer is assumed for the ophthalmic imaging apparatus 100 illustrated in FIG. 1, the present embodiment is not limited thereto. For example, a Michelson interferometer may be assumed for the ophthalmic imaging apparatus 100. Moreover, although the ophthalmic imaging apparatus 100 illustrated in FIG. 1 is configured to change the optical path length of the reference light, this embodiment is not limited thereto, but the ophthalmic imaging apparatus 100 may be configured to change the optical path length of the measuring light, for example.

Furthermore, although the description has been made on the case where the fundus Er is used as an imaging target site of the eye to be inspected E in this embodiment, the present invention is not limited thereto, but, for example, an anterior segment of eye can be used as an imaging target site of the eye to be inspected E.

In the ophthalmic imaging apparatus 100 according to this embodiment, the area setting portion 163 is configured to set one of the following imaging areas as the imaging area of the eye to be inspected E according to the maximum imageable area: the imaging area 214 (the first imaging area), which is a specified rectangular area; and the imaging area 314 (the second imaging area), which is narrower than the specified rectangular area and includes a curved part based on the maximum imageable area.

According to this configuration, not only the imaging area, which is a rectangular area, but also an imaging area including a curved part based on the maximum imageable area can be set according to the maximum imageable area. This enables the setting of the imaging area 314, which is wider than a rectangular area inscribed in the maximum imageable area 312 illustrated in FIG. 3, thereby enabling the acquisition of a wider range of image.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-213551, filed Oct. 31, 2016, which is hereby incorporated by reference herein in its entirety.

What is claimed is:

1. An ophthalmic imaging apparatus comprising:
a scanning unit which performs two-dimensional scanning on an eye to be inspected with measuring light based on light emitted from a light source;
a focus adjusting unit which adjusts a focus state in the measuring light to the eye to be inspected;
an image forming unit which forms an image related to imaging of the eye to be inspected, based on return light of the measuring light from the eye to be inspected;
a display control unit which performs control to display the image formed by the image forming unit on a display portion;
a setting unit which sets, as an imaging area of the eye to be inspected, one of imaging areas including a first imaging area and a second imaging area, wherein the setting unit sets the first imaging area to be defined by a rectangular area, in a case that the rectangular area is within an imageable area determined in accordance with the focus state, and sets the second imaging area to be defined by the rectangular area and the imageable area in a case that a partial area of the rectangular area is outside the imageable area,
wherein the display control unit controls the display portion (a) to display, in a case where the first imaging area is set, an image of the eye to be inspected corresponding to the first imaging area, and (b) to display, in a case where the second imaging area is set, an image of the eye to be inspected corresponding to the second imaging area, the image corresponding to the first imaging area and the image corresponding to the second imaging area being obtained by commonly using the scanning unit,
wherein a change of the imaging area of the eye to be inspected is performed by using an optical member included in the focus adjusting unit without changing a scanning area of the measuring light, which is controlled by the scanning unit, and
wherein the display control unit controls the display portion to display an image of the eye to be inspected corresponding to the second imaging area, the image corresponding to the second imaging area being obtained by changing at least a part of pixel values in the partial area of the rectangular area to a predetermined value, the partial area being outside the imageable area and including a part of a boundary defined by a shape of a lens, in a case that the rectangular area is larger than the imageable area having a shape including a curvature based on the lens.

2. The ophthalmic imaging apparatus according to claim 1, wherein:
the scanning unit performs the two-dimensional scanning on the eye to be inspected with the measuring light via a substantially circular lens;
the image forming unit forms the image, based on the return light having passed through the substantially circular lens and the scanning unit; and
the second imaging area includes a curved part based on the shape of the substantially circular lens.

3. The ophthalmic imaging apparatus according to claim 1, wherein, in the case where the setting unit sets the second imaging area, the image forming unit forms the image with a part outside the second imaging area in the rectangular area masked with the predetermined value.

4. The ophthalmic imaging apparatus according to claim 1, wherein, in the case where the setting unit sets the second imaging area and if the part outside the second imaging area in the rectangular area is larger than a predetermined threshold value, the image forming unit forms the image, based on the light of the part, with respect to the part.

5. The ophthalmic imaging apparatus according to claim 1, wherein the display control unit performs control to display the image based on the imaging area set by the setting unit on the display portion.

6. The ophthalmic imaging apparatus according to claim 1, further comprising a light amount control unit which controls the light amount of the measuring light, wherein, in the case where the setting unit sets the second imaging area, the light amount control unit performs control to decrease the light amount at least during a part of period during which the scanning unit scans the area outside the second imaging area.

7. The ophthalmic imaging apparatus according to claim 1, wherein:
the image forming unit further forms an observation image, based on the observation light output from an observation optical system for use in observing the eye to be inspected; and
the display control unit further performs control to superimpose the imaging area set by the setting unit on the observation image and to display the image on the display portion.

8. The ophthalmic imaging apparatus according to claim 1, further comprising:
a light dividing unit which divides the light emitted from the light source into the measuring light and reference light; and
a combining unit which combines the return light and the reference light,
wherein the image forming unit forms a tomographic image as the image, based on interference light combined by the combining unit.

9. The ophthalmic imaging apparatus according to claim 8, wherein the display control unit performs control to display at least three tomographic images aligned at the center position and both end positions in a sub scanning direction of the imaging area, which has been set by the setting unit, on the display portion, where the tomographic images are obtained by scanning the imaging area in a main scanning direction by the scanning unit, in the case where the scanning unit performs raster scanning as the two-dimensional scanning.

10. The ophthalmic imaging apparatus according to claim 1, wherein the setting unit is able to set the rectangular area until the rectangular area circumscribes the imageable area in the case where the scanning unit performs raster scanning as the two-dimensional scanning.

11. The ophthalmic imaging apparatus according to claim 1, wherein the scanning unit performs raster scanning or radial scanning as the two-dimensional scanning.

12. The ophthalmic imaging apparatus according to claim 1, wherein the second imaging area is narrower than the first imaging area and includes a curved part based on the imageable area.

13. The ophthalmic imaging apparatus according to claim 1, wherein the rectangular area is indicated, as an area desired to be imaged, on an observation image of the eye to be inspected.

14. The ophthalmic imaging apparatus according to claim 1, wherein the partial area includes at least one of four corners of the rectangular area.

15. A control method of an imaging apparatus, the control method comprising:
   adjusting a focus state in measuring light to an object irradiated with the measuring light;
   setting, as an imaging area of the object, one of imaging areas including a first imaging area and a second imaging area, the second imaging area (a) being different in a shape from the first imaging area and (b) having a shape defined based on a rectangular area and an imageable area determined in accordance with the focus state; and
   controlling a display unit (a) to display, in a case where the first imaging area is set, an image of the object corresponding to the first imaging area, and (b) to display, in a case where the second imaging area is set, an image of the object corresponding to the second imaging area, the image corresponding to the first imaging area and the image corresponding to the second imaging area being obtained by commonly using a scanning unit, the scanning unit being used for scanning the object with measuring light,
   wherein a change of the imaging area of the object is performed by using an optical member used for adjusting the focus state without changing a scanning area of the measuring light, which is controlled by the scanning unit, and
   wherein the display unit is controlled to display an image of the object corresponding to the second imaging area, the image corresponding to the second imaging area being obtained by changing at least a part of pixel values in the partial area of the rectangular area to a predetermined value, the partial area being outside the imageable area and including a part of a boundary defined by a shape of a lens, in a case that the rectangular area is larger than the imageable area having a shape including a curvature based on the lens.

16. A non-transitory tangible medium having recorded thereon a program for causing a computer to perform a method for controlling an imaging apparatus, the method comprising:
   adjusting a focus state in measuring light to an object irradiated with the measuring light;
   setting, as an imaging area of the object, one of imaging areas including a first imaging area and a second imaging area, the second imaging area (a) being different in a shape from the first imaging area and (b) having a shape defined based on a rectangular area and an imageable area determined in accordance with the focus state; and
   controlling a display unit (a) to display, in a case where the first imaging area is set, an image of the object corresponding to the first imaging area, and (b) to display, in a case where the second imaging area is set, an image of the object corresponding to the second imaging area, the image corresponding to the first imaging area and the image corresponding to the second imaging area being obtained by commonly using a scanning unit, the scanning unit being used for scanning the object with measuring light,
   wherein a change of the imaging area of the object is performed by using an optical member used for adjusting the focus state without changing a scanning area of the measuring light, which is controlled by the scanning unit, and
   wherein the display unit is controlled to display an image of the object corresponding to the second imaging area, the image corresponding to the second imaging area being obtained by changing at least a part of pixel values in the partial area of the rectangular area to a predetermined value, the partial area being outside the imageable area and including a part of a boundary defined by a shape of a lens, in a case that the rectangular area is larger than the imageable area having a shape including a curvature based on the lens.

17. An apparatus comprising:
   a focus adjusting unit which adjusts a focus state in measuring light to an object irradiated with the measuring light;
   a setting unit which sets, as an imaging area of the object, one of imaging areas including a first imaging area and a second imaging area, the second imaging area (a) being different in a shape from the first imaging area and (b) having a shape defined based on a rectangular area and an imageable area determined in accordance with the focus state; and
   a display control unit which controls a display unit (a) to display, in a case where the first imaging area is set, an image of the object corresponding to the first imaging area, and (b) to display, in a case where the second imaging area is set, an image of the object corresponding to the second imaging area, the image corresponding to the first imaging area and the image corresponding to the second imaging area being obtained by commonly using a scanning unit, the scanning unit being used for scanning the object with measuring light,
   wherein a change of the imaging area of the object is performed by using an optical member included in the focus adjusting unit without changing a scanning area of the measuring light, which is controlled by the scanning unit, and
   wherein the display control unit controls the display unit to display an image of the object corresponding to the second imaging area, the image corresponding to the second imaging area being obtained by changing at least a part of pixel values in the partial area of the rectangular area to a predetermined value, the partial area being outside the imageable area and including a part of a boundary being defined by a shape of a lens, in a case that the rectangular area is larger than the imageable area having a shape including a curvature based on the lens.

18. The apparatus according to claim 17, wherein the rectangular area is indicated, as an area desired to be imaged, on an observation image of the object.

19. The apparatus according to claim 17, wherein the partial area includes at least one of four corners of the rectangular area.

20. An image processing apparatus comprising:
a setting unit which sets, as an imaging area of an object, one of imaging areas including a first imaging area and a second imaging area, the first imaging area being within a predetermined area, and the second imaging area (a) being different in a shape from the first imaging area and (b) having a shape defined by a boundary including at least a part of a boundary defining the predetermined area; and
a display control unit which controls a display unit (a) to display, in a case where the first imaging area is set, an image of the object corresponding to the first imaging area, and (b) to display, in a case where the second imaging area is set, an image of the object corresponding to the second imaging area, the image corresponding to the first imaging area and the image corresponding to the second imaging area being obtained by commonly using a scanning unit, the scanning unit being used for scanning the object with measuring light,
wherein a change of the imaging area of the object is performed by using an optical member without changing a scanning area of the measuring light, which is controlled by the scanning unit, and
wherein the display control unit controls the display unit to display an image of the object corresponding to the second imaging area, the image corresponding to the second imaging area being obtained by changing at least a part of pixel values in the partial area of the predetermined area to a predetermined value, the partial area being outside an area having a shape including a part of a curvature based on a lens and the at least the part of the boundary defining the predetermined area, in a case that the predetermined area is larger than the area having the shape including the part of the curvature based on the lens.

21. The image processing apparatus according to claim 20, wherein the at least a part of the boundary includes a curved part.

22. The image processing apparatus according to claim 20, wherein in a case that the second imaging area is set, after acquiring the image of the object from an area larger than the second imaging area, a part of the image of the object outside the predetermined area is masked.

23. The imaging processing apparatus according to claim 20, wherein the first imaging area is indicated, as an area desired to be imaged, on an observation image of the object.

24. The image processing apparatus according to claim 20, wherein the predetermined area has a rectangular shape, and
wherein the partial area includes at least one of four corners of the rectangular shape.

25. An image processing method comprising the steps of:
setting, as an imaging area of an object, one of imaging areas including a first imaging area and a second imaging area, the first imaging area being within a predetermined area, and the second imaging area (a) being different in a shape from the first imaging area, and (b) having a shape defined by a boundary including at least a part of a boundary defining the predetermined area; and
controlling a display unit (a) to display, in a case where the first imaging area is set, an image of the object corresponding to the first imaging area, and (b) to display, in a case where the second imaging area is set, an image of the object corresponding to the second imaging area, the image corresponding to the first imaging area and the image corresponding to the second imaging area being obtained by commonly using a scanning unit, the scanning unit being used for scanning the object with measuring light,
wherein a change of the imaging area of the object is performed by using an optical member without changing a scanning area of the measuring light, which is controlled by the scanning unit, and
wherein the display unit is controlled to display an image of the object corresponding to the second imaging area, the image corresponding to the second imaging area being obtained by changing at least a part of pixel values in the partial area of the predetermined area to a predetermined value, the partial area being outside an area having a shape including a part of a curvature based on a lens and the at least the part of the boundary defining the predetermined area, in a case that the predetermined area is larger than the area having the shape including the part of the curvature based on the lens.

26. A non-transitory computer-readable storage medium storing a program for causing a computer to execute the method according to claim 25.

27. An image processing apparatus comprising:
a setting unit which sets, as an imaging area of an object, one of imaging areas including a first imaging area and a second imaging area, the first imaging area being within an area of which a size is changeable, and the second imaging area being different in a shape from the first imaging area; and
a display control unit which controls a display unit (a) to display, in a case where the first imaging area is set, an image of the object corresponding to the first imaging area, and (b) to display, in a case where the second imaging area is set, an image of the object corresponding to the second imaging area,
wherein in a case where the display control unit controls the display unit to display the image of the object corresponding to the second imaging area, the image of the object corresponding to the second imaging area is obtained by changing, to a predetermined value, at least a part of pixel values in a partial area of the area of which size is changeable, the partial area being outside an area having a shape including a part of a curvature based on a lens.

28. The image processing apparatus according to claim 27, wherein in a case that the second imaging area is set, after acquiring an image corresponding to the second imaging area, an image corresponding to the partial area is masked.

29. The image processing apparatus according to claim 27, wherein the area of which a size is changeable has a rectangular shape, and
wherein the partial area includes at least one of four corners of the rectangular shape.

30. The image processing apparatus according to claim 27, wherein a change of the imaging area of the object is performed by using an optical member without changing a scanning area of measuring light.

31. An image processing method comprising the steps of:
setting, as an imaging area of an object, one of imaging areas including a first imaging area and a second imaging area, the first imaging area being within an area of which a size is changeable, and the second imaging area being different in a shape from the first imaging area; and controlling a display unit (a) to display, in a case where the first imaging area is set, an image of the object corresponding to the first imaging area, and (b) to display, in a case where the second imaging area is set, an image of the object corresponding to the second imaging area, wherein in a case where the display unit is controlled to display the image of the object corresponding to the second imaging area, the image of the object corresponding to the second imaging area is obtained by changing, to a predetermined value, at least a part of pixel values in a partial area of the area of which a size is changeable, the partial area being outside an area having a shape including a part of a curvature based on a lens.

32. A non-transitory computer-readable storage medium storing a program for causing a computer to execute the method according to claim 31.

33. An image processing apparatus comprising:
- a setting unit which sets one of a first imaging area and a second imaging area as an imaging area of an object based on (a) a scanning area to be scanned by a scanning unit, the scanning unit scanning the object with measurement light and being within an optical head portion which acquires an image of the object in the imaging area and (b) a predetermined area having a shape based on a lens of the optical head portion; and
- a display control unit which controls a display unit to display an image of the object corresponding to the imaging area, wherein the first imaging area is set as an area, within the predetermined area, having a shape identical to the scanning area, wherein the second imaging area is set as a portion of the scanning area within the predetermined area to have a different shape from the first imaging area, the second imaging area having at least a part of a boundary of the predetermined area, and wherein in a case that the second imaging area is set, the display control unit controls the display unit to display an image of the object corresponding to the second imaging area by changing, to a predetermined value, pixel values in another portion of the scanning area outside of the predetermined area.

34. The image processing apparatus according to claim 33, wherein in a case that the second imaging area is set, after acquiring an image corresponding to the second imaging area, an image corresponding to the another portion is masked.

35. The image processing apparatus according to claim 33, wherein the scanning area has a rectangular shape, and
wherein the another portion includes at least one of four corners of the rectangular shape.

36. The image processing apparatus according to claim 33, wherein the lens of the optical head portion corresponding to the shape of the predetermined area is an objective lens.

37. The image processing apparatus according to claim 33, wherein the predetermined area changes according to the position of a lens within the optical head portion.

38. The image processing apparatus according to claim 37, wherein the lens of the optical head portion corresponding to the change of the predetermined area is a focus lens.

39. The image processing apparatus according to claim 33, wherein the image of the object is a fundus front image.

40. The image processing apparatus according to claim 33, wherein the image of the object is a fundus tomographic image.

* * * * *